(12) United States Patent
Stamm et al.

(10) Patent No.: US 6,353,115 B1
(45) Date of Patent: Mar. 5, 2002

(54) METHOD FOR PRODUCING CARBONYL DIIMIDAZOLES

(75) Inventors: Armin Stamm, Mainz; Jochem Henkelmann, Mannheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/720,913

(22) PCT Filed: Jul. 6, 1999

(86) PCT No.: PCT/EP99/04729

§ 371 Date: Jan. 2, 2001

§ 102(e) Date: Jan. 2, 2001

(87) PCT Pub. No.: WO00/02863

PCT Pub. Date: Jan. 20, 2000

(30) Foreign Application Priority Data

Jul. 8, 1998 (DE) ......................... 198 30 556

(51) Int. Cl.$^7$ ............................ C07D 403/12
(52) U.S. Cl. ................................. 548/313.7
(58) Field of Search ........................ 548/313.7

(56) References Cited

U.S. PATENT DOCUMENTS

| | | | | |
|---|---|---|---|---|
| 3,868,458 A | * | 2/1975 | Baker et al. | 424/273 |
| 3,991,071 A | | 11/1976 | Brookes et al. | 260/309 |
| 4,957,933 A | * | 9/1990 | Geffken et al. | 514/376 |
| 5,552,554 A | | 9/1996 | Sternberg et al. | 548/226 |
| 5,559,233 A | * | 9/1996 | Bernhart et al. | 544/321 |

FOREIGN PATENT DOCUMENTS

| | | | |
|---|---|---|---|
| EP | 692 476 | | 1/1996 |
| WO | WO 98/31672 | | 7/1998 |
| WO | 00/06551 | * | 2/2000 |

OTHER PUBLICATIONS

Stabb, H.A. and Wendel, K., Organic Synth. Coll. , vol. v., pp. 201–214., 1973.*

* cited by examiner

*Primary Examiner*—Floyd D. Higel
*Assistant Examiner*—Golam M. M. Shameem
(74) *Attorney, Agent, or Firm*—Keil & Weinkauf

(57) ABSTRACT

In a process for preparing carbonyldiimidazole of the general formulae Ia, Ib, Ic or mixtures thereof

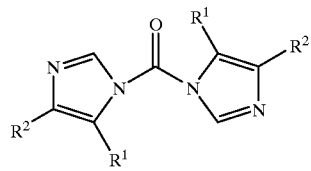

(Ia)

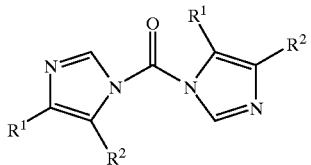

(Ib)

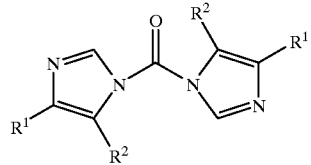

(Ic)

where $R^1$ is hydrogen or a $C_{1-4}$-alkyl radical and $R^2$ is hydrogen or a methyl radical, by reacting at least one imidazole of the general formulae IIa and IIb

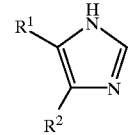

(IIa)

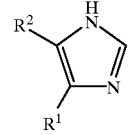

(IIb)

in which $R^1$ and $R^2$ have the abovementioned meaning, with phosgene in an inert solvent, stoichiometric amounts, based on the imidazoles, of an organic nitrogen base which has a lower $pK_b$ than imidazole are added to the reaction mixture.

5 Claims, No Drawings

METHOD FOR PRODUCING CARBONYL DIIMIDAZOLES

The present invention relates to an improved process for preparing carbonyldiimidazoles from imidazoles and phosgene avoiding the coupling product imidazole hydrochloride.

Carbonyldiimidazole (CDI) is a reagent frequently used for introducing carbonyl groups, for example for preparing carbonates, ureas or urethanes, or for activating unreactive reactants in ester or amide synthesis (Angew. Chem. 74 (1962), 407).

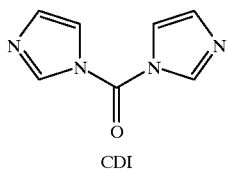

CDI

Two ways of preparing carbonyldiimidazole are known in principle. Chem. Ber. 93 (1960), 2804 and U.S. Pat. No. 4,965,366 describe a two-stage process in which firstly imidazole is reacted with trimethylsilyl chloride to give 1-trimethylsilylimidazole, and the latter is then reacted with phosgene as shown in the following scheme to give CDI.

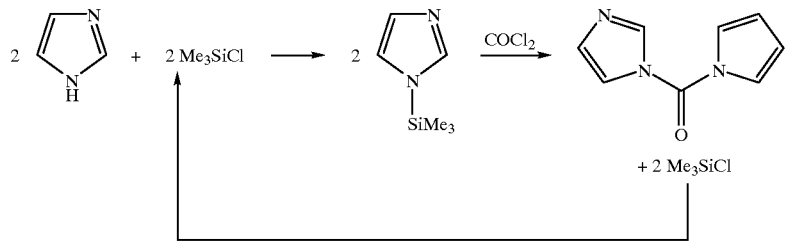

Although the trimethylsilyl chloride can be circulated for reuse, the time consumption for this synthetic route is considerable, resulting in a poor space-time yield of the required product. In addition, the handling of the hydrolysis-sensitive trimethylsilyl chloride makes additional demands on the reaction apparatus.

The more elegant way of preparing CDI is the direct phosgenation of imidazole which was originated by Staab et al. and is described in various publications (Liebigs Ann. Chem. 609 (1957), 75; Chem. Ber. 96 (1963), 3374; Org. Synth. Coll. Vol. V (1973), 201). Although this results in two moles of imidazole hydrochloride per mole of CDI as coupling product, the former can be converted by basic work-up back into imidazole and returned to the phosgenation:

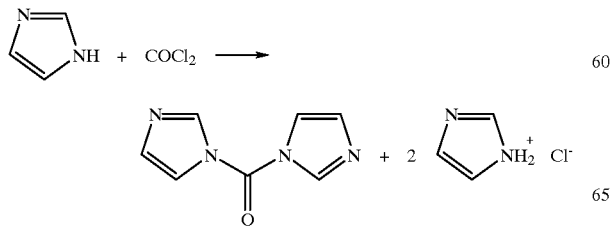

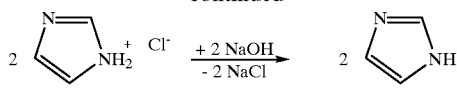

EP-A-0 692 476 extends the synthetic route described in the previous references merely by a method for dehydrating the solvent. However, one considerable difficulty of the original methods remains. The imidazole hydrochloride also formed as coupling product must be removed from the CDI-containing reaction solution by filtration with exclusion of moisture at high temperatures (80 to 100° C.). Great technical complexity is necessary for maintaining a sufficiently high quality of product because the CDI is extremely sensitive to hydrolysis.

The disadvantage of all processes to date for the direct phosgenation of imidazole is the formation of the coupling product imidazole hydrochloride, which must be recycled in an additional process stage and which leads to a halving of the space-time yield.

WO 98/31672, which has an earlier priority but is not a prior publication, relates to a process for preparing, for example, CDI by reacting, for example, imidazole with phosgene in the presence of an organic base, e.g. tri(n-butyl) amine.

It is an object of the present invention to provide a process for preparing carbonyldiimidazoles from imidazoles and phosgene which avoids the disadvantages mentioned.

We have found that this object is achieved by a process for preparing carbonyldiimidazoles of the general formulae Ia, Ib, Ic or mixtures thereof

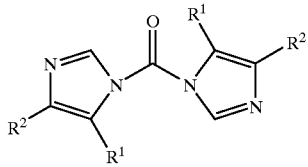
(Ia)

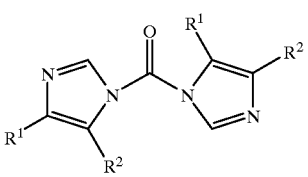
(Ib)

-continued

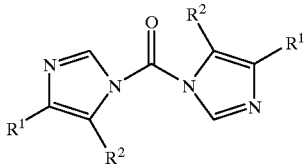

(Ic)

where $R^1$ is hydrogen or a $C_{1-4}$-alkyl radical and $R^2$ is hydrogen or a methyl radical, by reacting at least one imidazole of the general formulae IIa and IIb

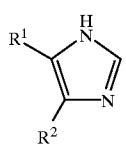

(IIa)

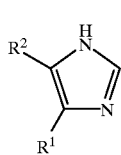

(IIb)

in which $R^1$ and $R^2$ have the abovementioned meaning, with phosgene in an inert solvent, adding to the reaction mixture, based on the imidazoles, stoichiometric amounts or an excess of up to 30 mol % of an organic nitrogen base which has a lower $pK_b$ than imidazole.

In the process, the formation of imidazole hydrochloride is avoided by the addition of an organic base, so that the imidazole employed can be completely converted into the carbonyldiimidazole. With this management of the synthesis, the hydrochloric acid which inevitably results as by-product is bound by a stronger base than imidazole, so that all the imidazole employed can react to give the carbonyldiimidazole. It is then only necessary to separate the hydrochloride of the auxiliary base from the product for conversion into the free base and recycling into the synthesis.

Imidazole itself is a weak base ($pK_b$ about 7) and acts both as reagent and as acid trap in the phosgenation reaction. On addition of a stronger nitrogen base, for example a tertiary aliphatic amine, in particular tributylamine, during the synthesis there is either immediate preferential protonation of the stronger base, or re-formation of imidazole from the hydrochloride formed:

The imidazole which is thereby once again in the form of the free base can be further phosgenated. In order to ensure complete conversion of all the imidazole employed, according to the following overall equation an equivalent amount of tertiary nitrogen base is necessary.

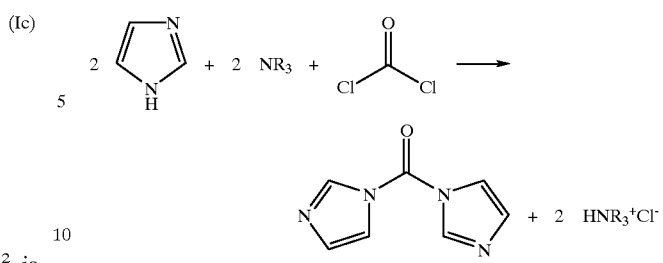

The advantage of the process is, inter alia, that the space-time yield is twice that of the processes described previously, because the imidazole employed is completely converted and there is no need to recycle the unused half of the imidazole as hydrochloride.

The reaction is carried out in an inert solvent, preferably at a temperature in the range from 60 to 100° C., particularly preferably at 60 to 80° C., in a substituted aromatic hydrocarbon. Xylene or chlorobenzene is preferably employed for this, and xylene can be in the form of a mixture of o-, m- and p-xylene or of one of the isomers. Xylene or mixtures of its isomers are particularly preferably employed.

A suitable tertiary nitrogen base is in principle any base with a $pK_b$ which is lower than the $pK_b$ of imidazole.

It is preferred to employ as nitrogen base a tertiary amine of the general formula $NR_3$ where the R radicals are each, independently of one another, branched or unbranched $C_{1-10}$-alkyl, or two of the radicals form with one nitrogen atom a 5- or 6-membered heterocyclo-aliphatic or heteroaromatic ring which may additionally be interrupted by one or two oxygen or nitrogen atoms.

The nitrogen base is preferably a tertiary aliphatic amine in which the R radicals are identical and are $C_{1-4}$-alkyl radicals, such as trimethyl-, triethyl-, tripropyl-, triisopropyl-, tri-n-butyl-, triisobutyl-, tri-sec-butylamine. Tri-n-butylamine is particularly preferred. Examples of amines in which two of the radicals produce a ring are N-alkylpyrrolidines and N-alkylpiperidines. Examples of rings interrupted by hetero atoms are given by N-alkylmorpholines and N,N'-dialkylpiperazines.

The procedure is described below for the example of carbonyldiimidazole (CDI). However, the process can also be employed for the abovementioned substituted compounds.

It is expected that the amine hydrochloride which is formed ought to precipitate out of the reaction mixture as solid phase. In the described process, the reaction solution remains homogeneous at elevated temperatures (50 to 60° C.). Only on cooling does carbonyldiimidazole precipitate from the reaction mixture in colorless needles, while the tributylamine hydrochloride remains completely in the solvent. Without being bound to one theory, it is evident that the CDI is displaced from the solution by the amine hydrochloride by a salting-out effect, while the tributylamine hydrochloride remains dissolved, because of its longer and polar alkyl radicals, in the solvent.

The CDI which is formed can be crystallized out by cooling the reaction mixture and be removed as solid, while the hydrochloride which is formed from the nitrogen base remains in the organic solution. The precipitated CDI can be removed from the solvent/amine hydrochloride mixture by simple filtration with suction under inert gas or by removal using a centrifuge. It is sufficiently pure for further uses even without washing. This is a considerable advantage of the process because the product, which is very sensitive to moisture, comes into contact with air only once. The hydrochloride of the tertiary amine which is dissolved in the solvent can be neutralized with a stronger aqueous inorganic base, preferably an aqueous solution of NaOH or KOH, to return to the free base, which remains in the organic solvent. The liberated nitrogen base in the organic solvent can then be separated from the aqueous phase and recycled to the synthesis.

The invention is illustrated further by means of examples below.

EXAMPLE 1

All the reactions are carried out in a HWS vessel with a capacity of 2 l, jacket heating and a carbon dioxide condenser (−78° C.) and stirrer.

185.4 g of tributylamine (1 mol) are dissolved in 1010 g of xylene. The solution is heated to reflux, and xylene is distilled into a water trap until water no longer separates out (total about 10 ml). After adding 68 g (1 mol) of imidazole to the reaction mixture, a total of 51 g (0.5 mol) of phosgene is passed in at 68 to 80° C. over the course of 30 minutes. After the end of the addition, the reaction is allowed to continue at 65° C. for 60 minutes. The homogeneous discharge from the reaction is transferred into an Erlenmeyer flask flushed with dry argon. After cooling at room temperature, colorless crystals separate out after a short time and are filtered off with suction under argon and washed twice with 50 ml of dry xylene each time. After drying in vacuo, 59 g of CDI of melting point 112° C. are obtained.

Elemental analysis: calculated: C: 51.84 H: 3.74 N: 34.56. found: C: 51.90 H: 3.80 N: 34.60.

EXAMPLE 2

Recycling of the tributylamine hydrochloride with renewed reaction 40% strength sodium hydroxide solution is added to the stirred mother liquor from Example 1 until the pH remains constant at 12 (total: g). The aqueous (lower) phase is separated off, the xylene solution of tributylamine (upper phase) is transferred into the reaction vessel, and xylene is distilled into a water trap until water no longer separates out. After cooling the reaction mixture, 68 g (1 mol) of xylene and 21 g (0.1 mol) of tributylamine are added.

At 72 to 83° C., a total of 51 g (0.5 mol) of phosgene is passed in over the course of 30 minutes. After the metering in of phosgene is complete, stirring is continued at 65° C. for 60 minutes. Working-up is carried out as in Example 1. After drying, 57 g of CDI of melting point 112° C. are obtained.

EXAMPLE 3

The mother liquor from Example 2 is worked up by a procedure analogous to that described in Example 2 and is phosgenated at 70 to 79° C. After work-up, 53 g of CDI of melting point 109° C. are obtained.

EXAMPLE 4

Repetition of Example 1

185.4 g of tributylamine (1 mol) are dissolved in 1010 g of xylene. The solution is heated to reflux, and xylene is distilled into a water trap until water no longer separates out (total about 10 ml). After adding 68 g (1 mol) of imidazole to the reaction mixture, a total of 56 g (0.57 mol) of phosgene is passed in at 68 to 78° C. over the course of 30 minutes. After the end of the addition, the reaction is allowed to continue at 65° C. for 60 minutes. The homogeneous discharge from the reaction is transferred into an Erlenmeyer flask flushed with dry argon. After cooling at room temperature, colorless crystals separate out after a short time and are filtered off with suction under argon and washed twice with 50 ml of dry xylene each time. After drying in vacuo, 62 g of CDI of melting point 114° C. are obtained.

EXAMPLE 5

The synthesis is carried out as in Examples 1 and 4 using chlorobenzene as solvent. With an identical procedure and work-up, 50 g of CDI of melting point 114° C. are obtained.

We claim:
1. A process for preparing carbonyldiimidazoles of the formulae Ia, Ib, Ic or mixtures thereof

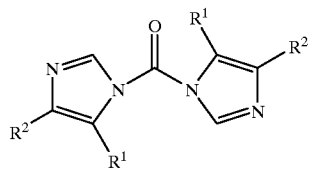

(Ia)

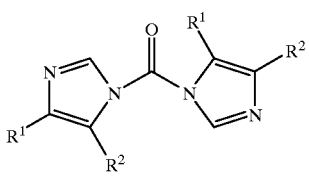

(Ib)

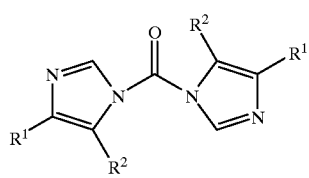

(Ic)

where $R^1$ is hydrogen or a $C_{1-4}$-alkyl radical and $R^2$ is hydrogen or a methyl radical, by reacting at least one imidazole of the formulae IIa and IIb

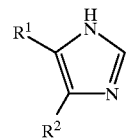

(IIa)

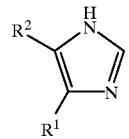

(IIb)

in which $R^1$ and $R^2$ have the abovementioned meaning, with phosgene in an inert solvent, which comprises adding to the reaction mixture, based on the imidazoles, stoichiometric amounts of an organic nitrogen base which has a lower $pK_b$ than imidazole, wherein the carbonyldiimidazole which is formed is crystallized out by cooling the reaction mixture and is removed as solid, while the hydrochloride which is formed from the nitrogen base remains in the organic solution, the hydrochloride of the nitrogen base is neutralized with a stronger aqueous organic base to return to the free base, which remains in the organic solvent, and wherein the liberated nitrogen base in the organic solvent is separated from the aqueous phase and recycled to the synthesis, wherein the nitrogen base employed is a tertiary amine of the general formula $NR_3$ where the R radicals are each, independently of one another, branched or unbranched $C_{1-10}$-alkyl, or two of the radicals form with one nitrogen atom a 5- or 6-membered heterocycloaliphatic or heteroaromatic ring.

2. A process as claimed in claim 1, wherein the nitrogen base is a tertiary aliphatic amine in which the R radicals are identical and are $C_{1-4}$-alkyl radicals.

3. A process as claimed in claim 2, wherein the tertiary aliphatic amine is tri-n-butylamine.

4. A process as claimed in claim 1, wherein a substituted aromatic hydrocarbon is used as solvent.

5. A process as claimed in claim 4, wherein o-xylene or mixtures of o, m and p-xylene isomers are used as solvent.

* * * * *

UNITED STATES PATENT AND TRADEMARK OFFICE
CERTIFICATE OF CORRECTION

PATENT NO. : 6,353,115 B1 Page 1 of 1
DATED : March 5, 2002
INVENTOR(S) : Stamm et al.

It is certified that error appears in the above-identified patent and that said Letters Patent is hereby corrected as shown below:

Column 6,
Line 59, "stronger aqueous organic base" should be -- stronger aqueous inorganic base --.

Signed and Sealed this

Twenty-third Day of July, 2002

Attest:

Attesting Officer

JAMES E. ROGAN
Director of the United States Patent and Trademark Office